United States Patent [19]
Brattesani

[11] Patent Number: 5,692,642
[45] Date of Patent: Dec. 2, 1997

[54] FLUID DISPENSER ADAPTER AND METHOD OF USE

[76] Inventor: Steven J. Brattesani, 2561 Chestnut St., San Francisco, Calif. 94123

[21] Appl. No.: 543,176

[22] Filed: Oct. 5, 1995

[51] Int. Cl.⁶ ........................................................ B67D 5/46
[52] U.S. Cl. ........................... 222/1; 222/326; 222/327; 222/391; 433/90
[58] Field of Search ........................ 222/326, 327–389, 222/391, 174; 433/89, 90; 604/209, 218, 228, 232–235

[56] References Cited

U.S. PATENT DOCUMENTS

| | | | |
|---|---|---|---|
| D. 357,536 | 4/1995 | Dragan et al. . | |
| 3,110,310 | 11/1963 | Cislak | 604/209 |
| 3,141,583 | 7/1964 | Mapel et al. | 222/327 X |
| 3,319,839 | 5/1967 | Cox | 222/391 X |
| 3,726,440 | 4/1973 | Deeb | 222/327 X |
| 3,768,472 | 10/1973 | Hodosh et al. | 222/389 X |
| 4,099,548 | 7/1978 | Sturm et al. | 222/391 X |
| 4,264,305 | 4/1981 | Rasmussen et al. | 433/90 |
| 4,330,070 | 5/1982 | Doubleday | 222/326 X |
| 4,330,280 | 5/1982 | Dougherty et al. . | |
| 4,360,332 | 11/1982 | Cyin | 222/389 X |
| 4,384,853 | 5/1983 | Welsh . | |
| 4,444,560 | 4/1984 | Jacklich | 222/391 X |
| 4,472,141 | 9/1984 | Dragan | 433/90 |
| 4,738,664 | 4/1988 | Prindle | 604/228 |
| 5,015,233 | 5/1991 | McGough et al. | 222/389 X |
| 5,306,147 | 4/1994 | Dragan et al. . | |
| 5,444,523 | 8/1995 | Fischer et al. . | |

OTHER PUBLICATIONS

Miltex Aspirating Syringe "C–W" Type, Ide Interstate Inc. Dental Supply Catalog, Fall 1994/Winter 1995, P. 12.
Miltex N–Tralig® Intraligamental Anesthesia Syringe, Miltex Catalog #76–50, Undated.

*Primary Examiner*—Kevin P. Shaver
*Attorney, Agent, or Firm*—John P. O'Banion

[57] ABSTRACT

A dispenser adapter apparatus which allows dispensing of multiple types of materials with use of a single dispensing device. The invention includes a cartridge holder with a socket for receiving a replaceable cartridge of adhesive, filler, or other material. The cartridge holder is reversibly coupled to a dispensing device such as a syringe or dispensing gun. A plunger associated with the cartridge holder forces material from the cartridge. Force is transferred from the piston of the dispensing device to the plunger of the dispenser adapter apparatus by mechanically interfacing the piston and plunger.

21 Claims, 12 Drawing Sheets

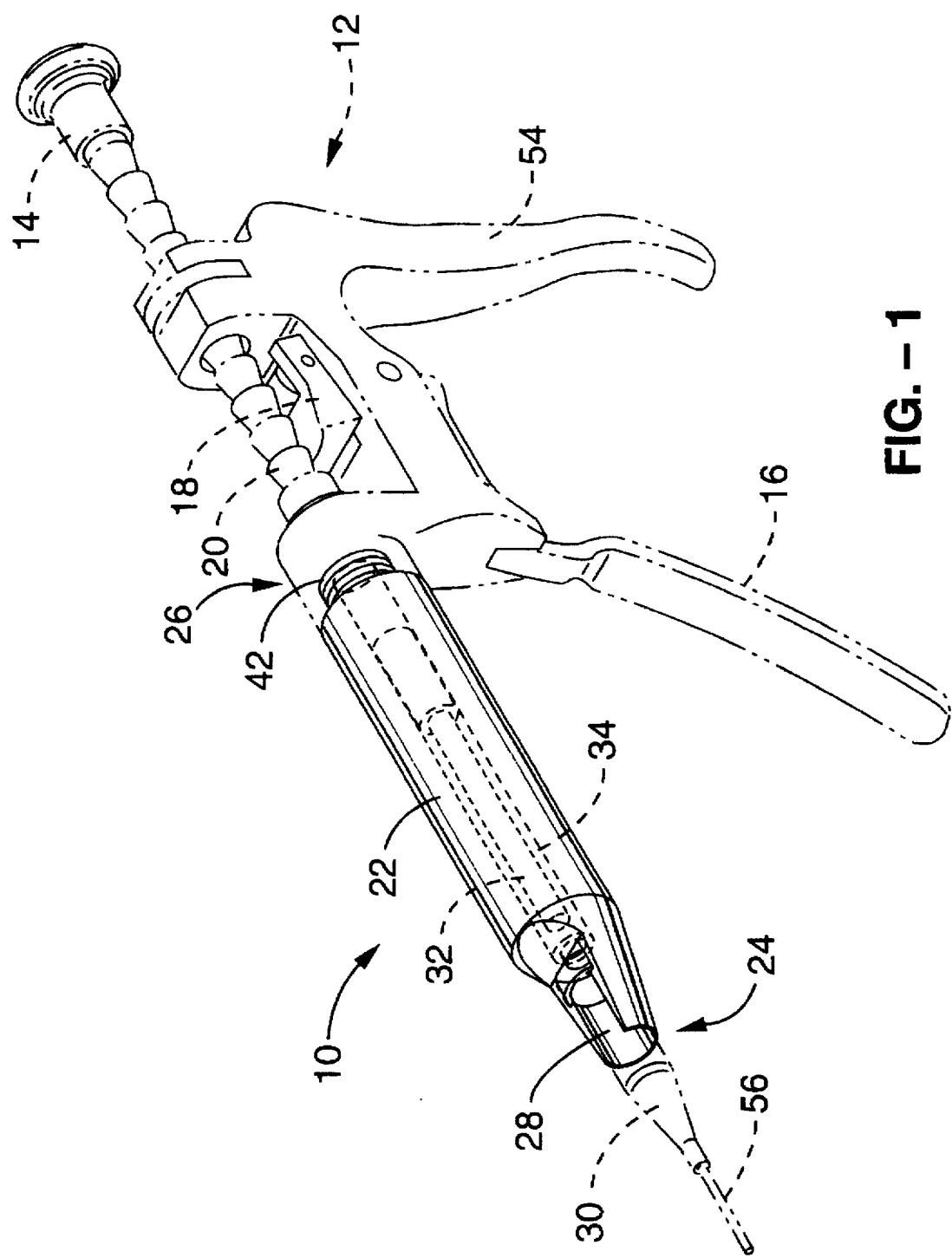
FIG. —1

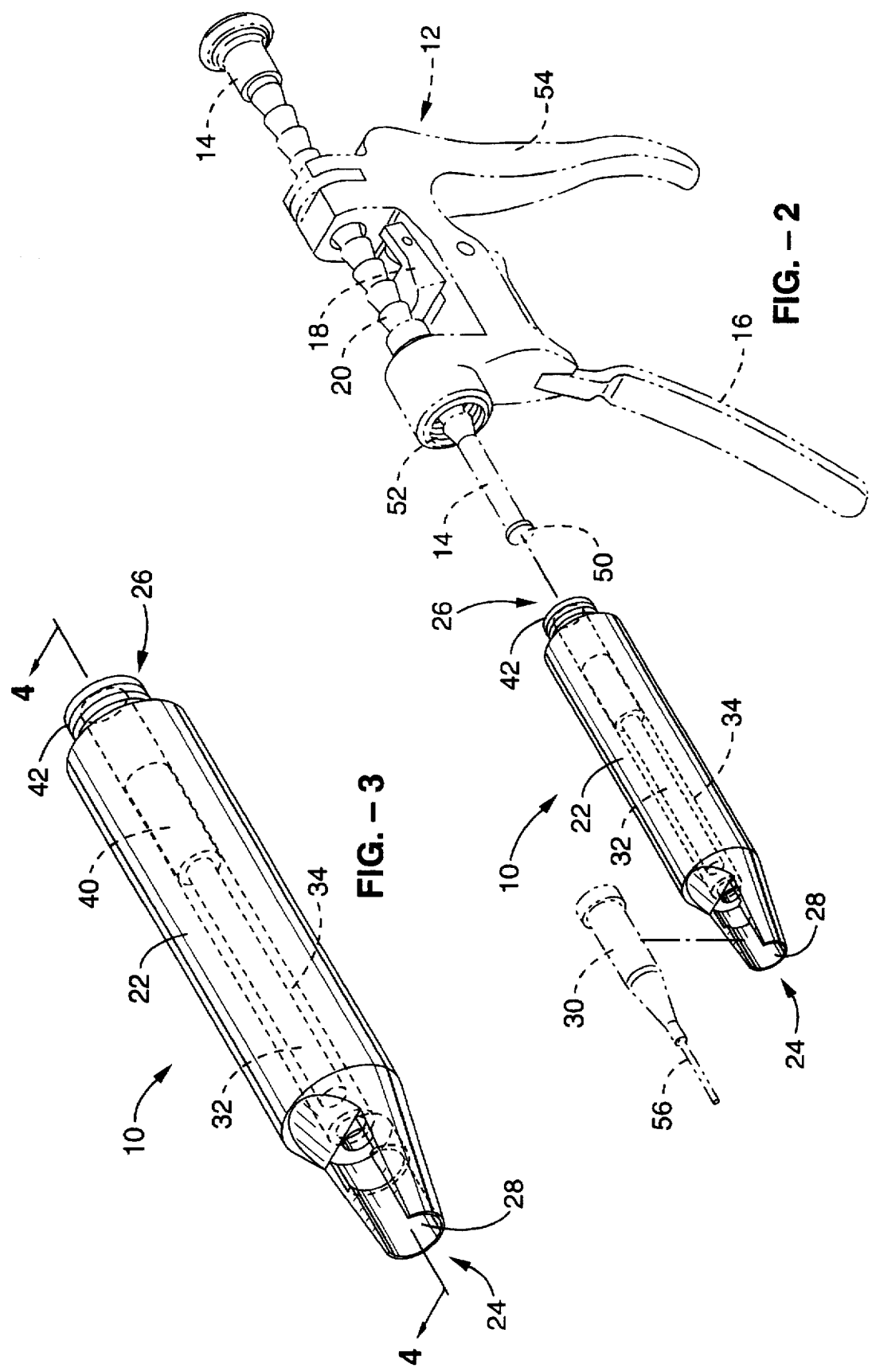

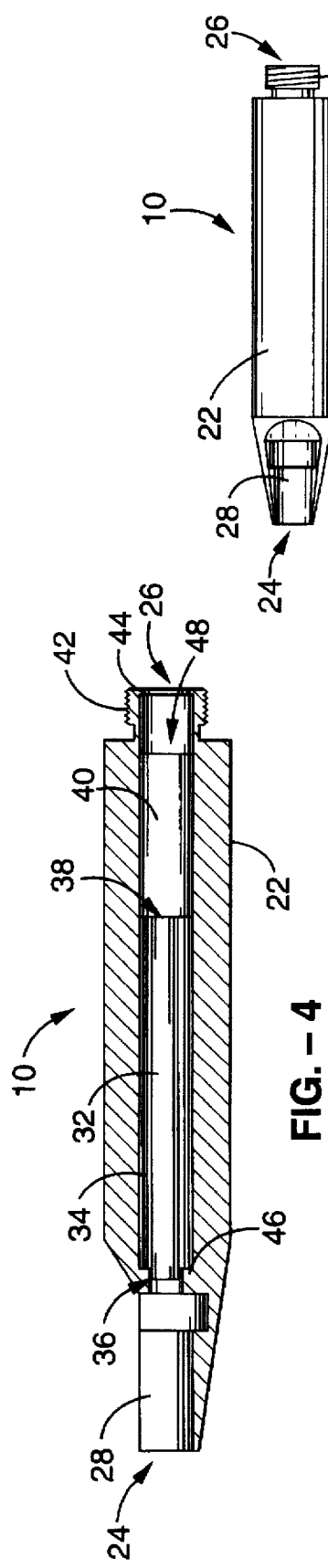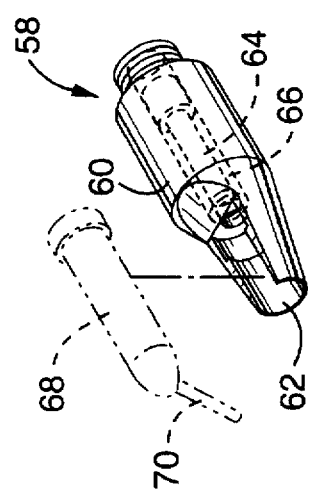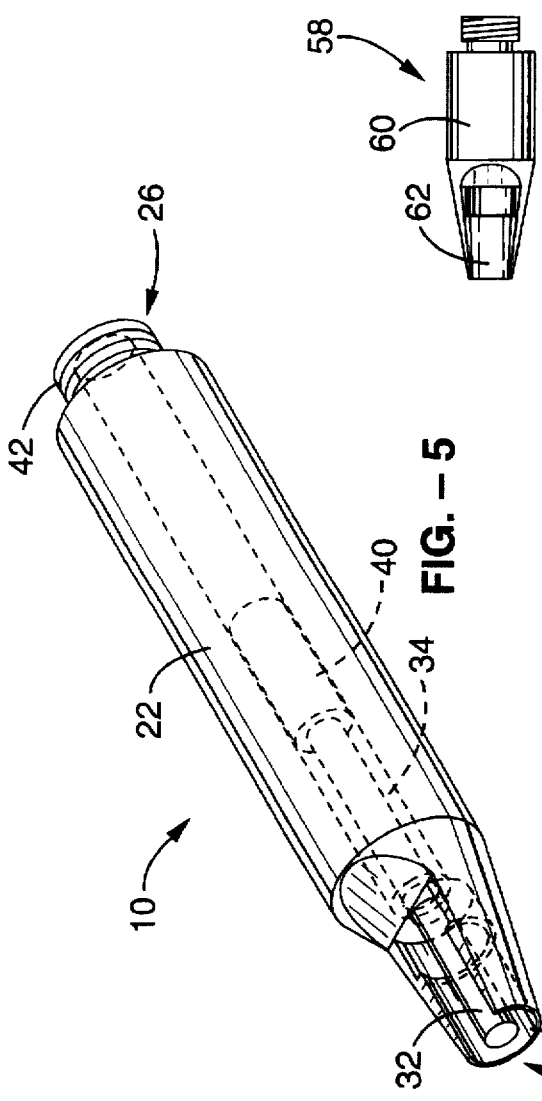

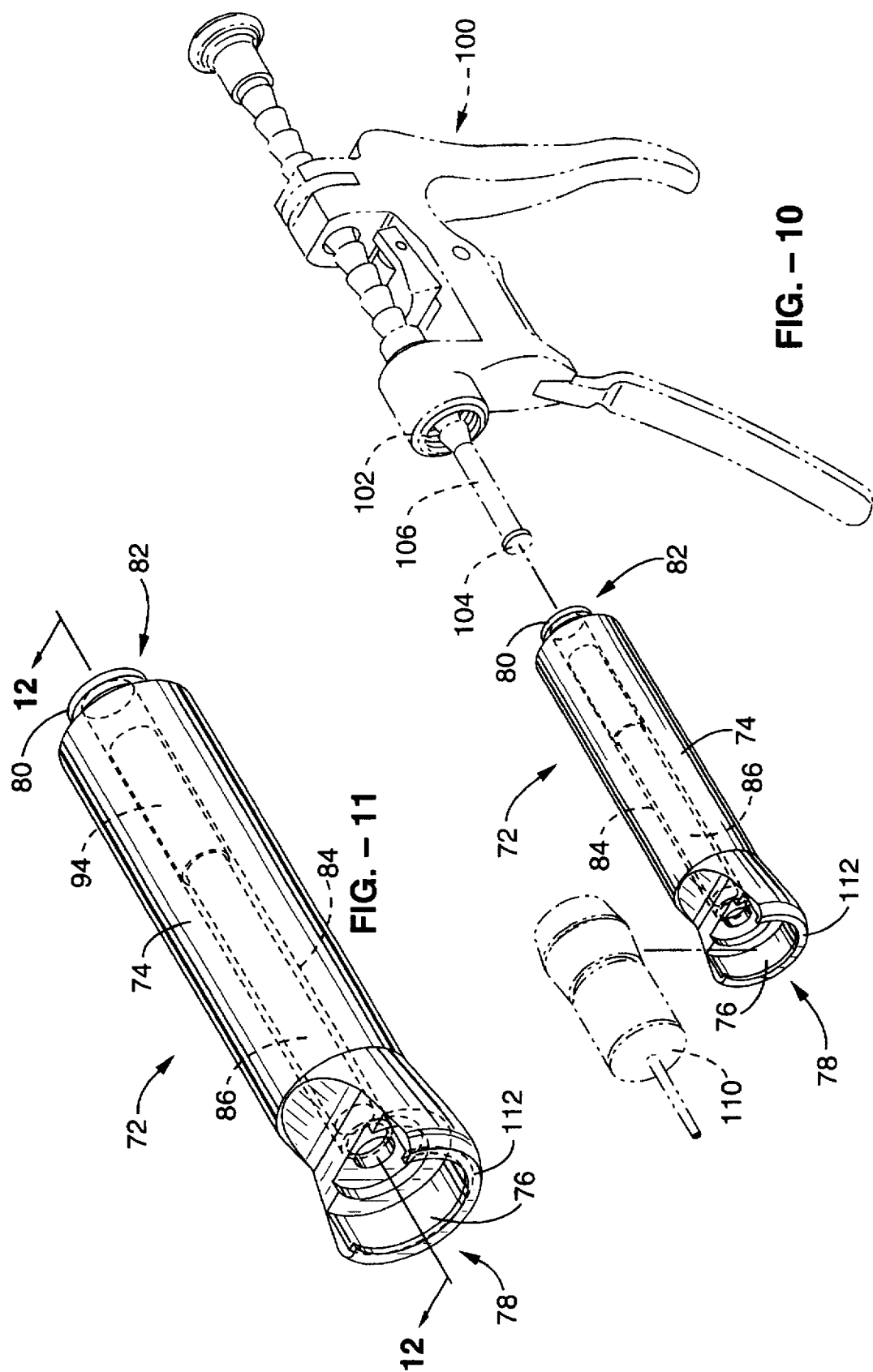

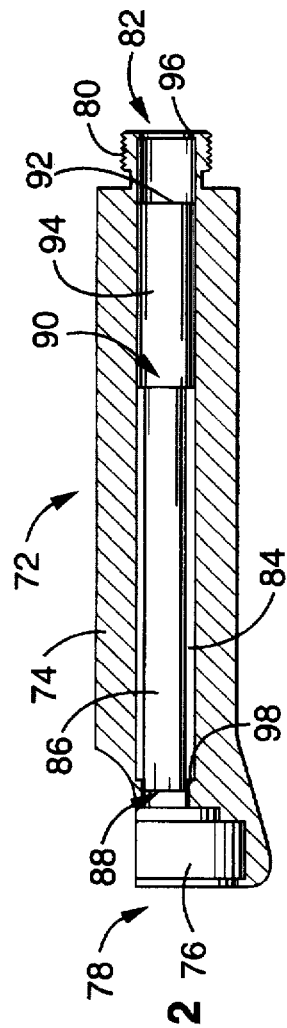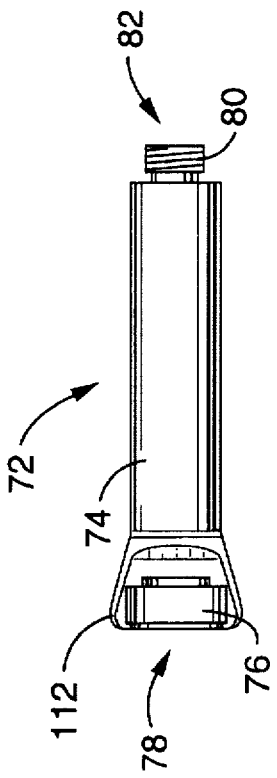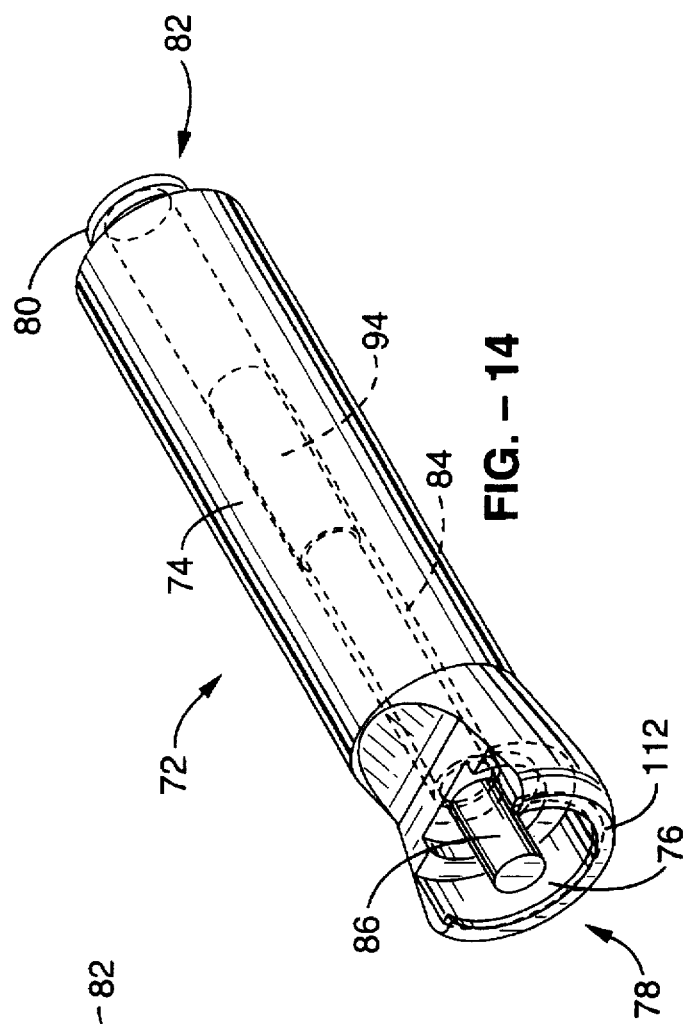

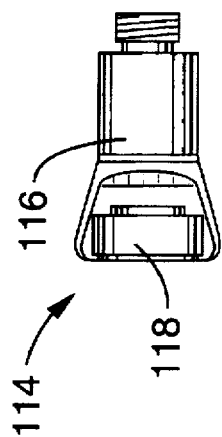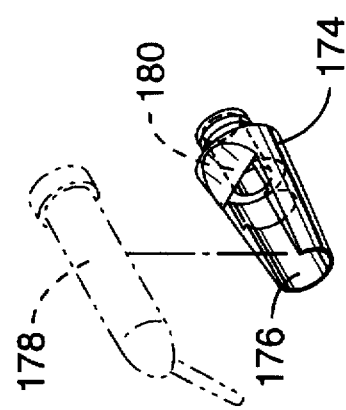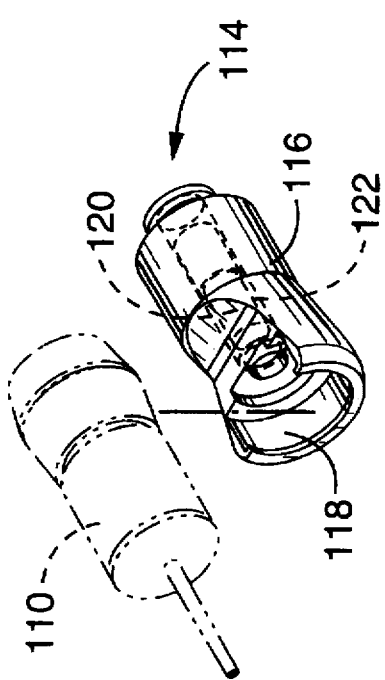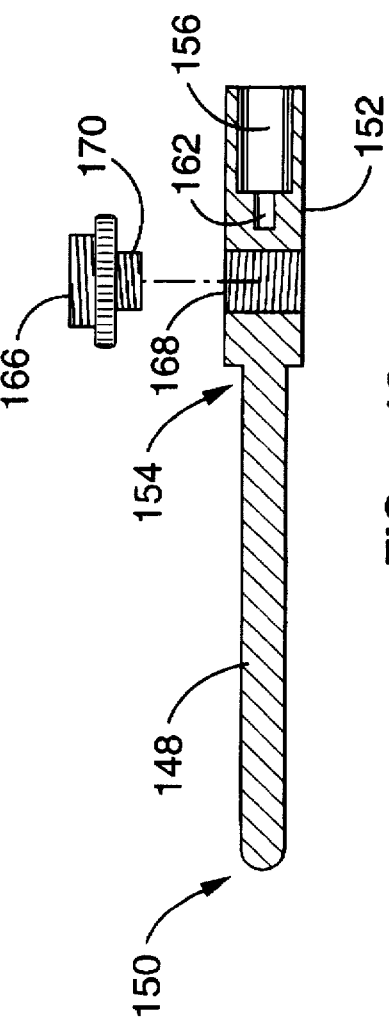

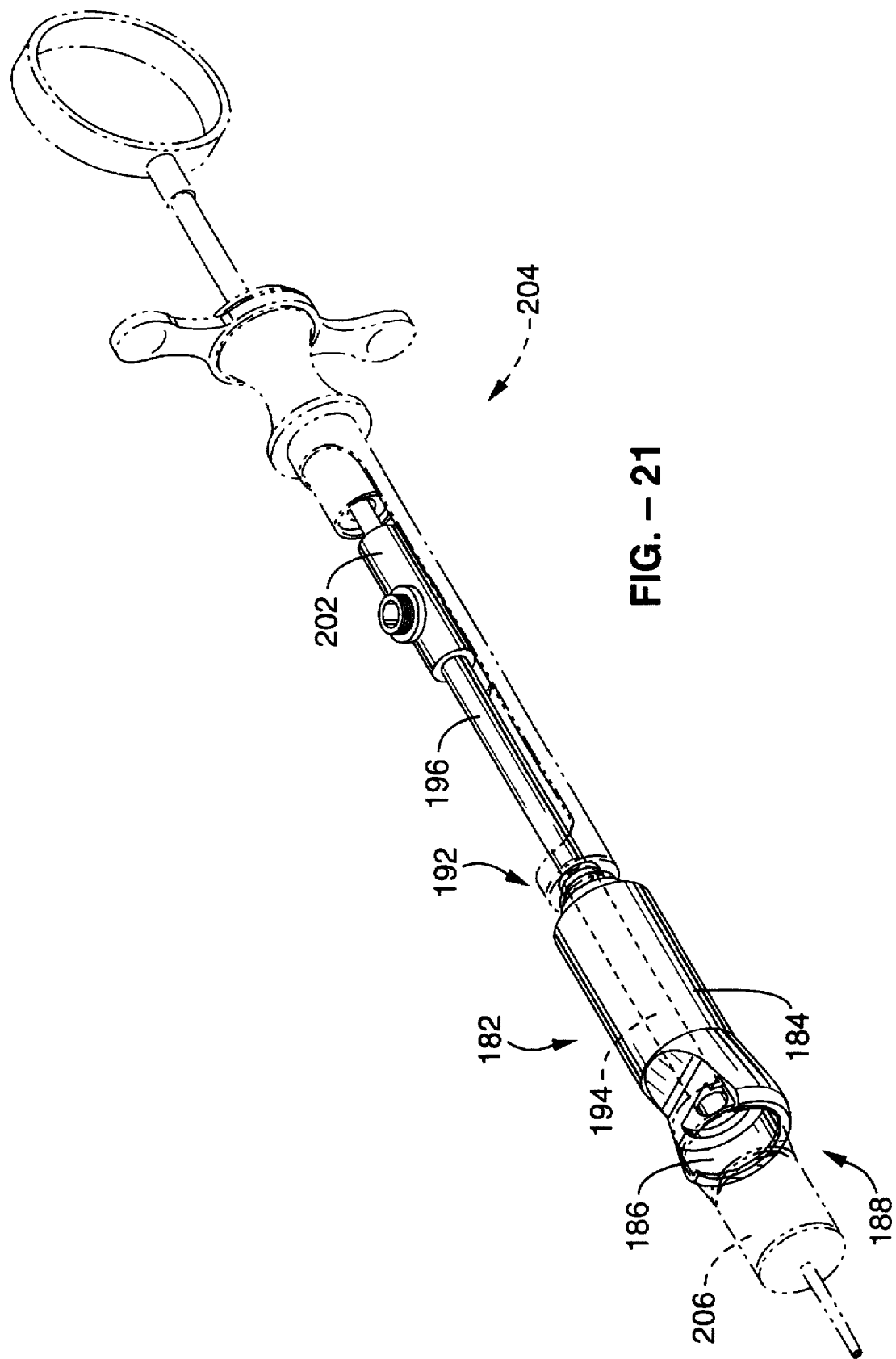

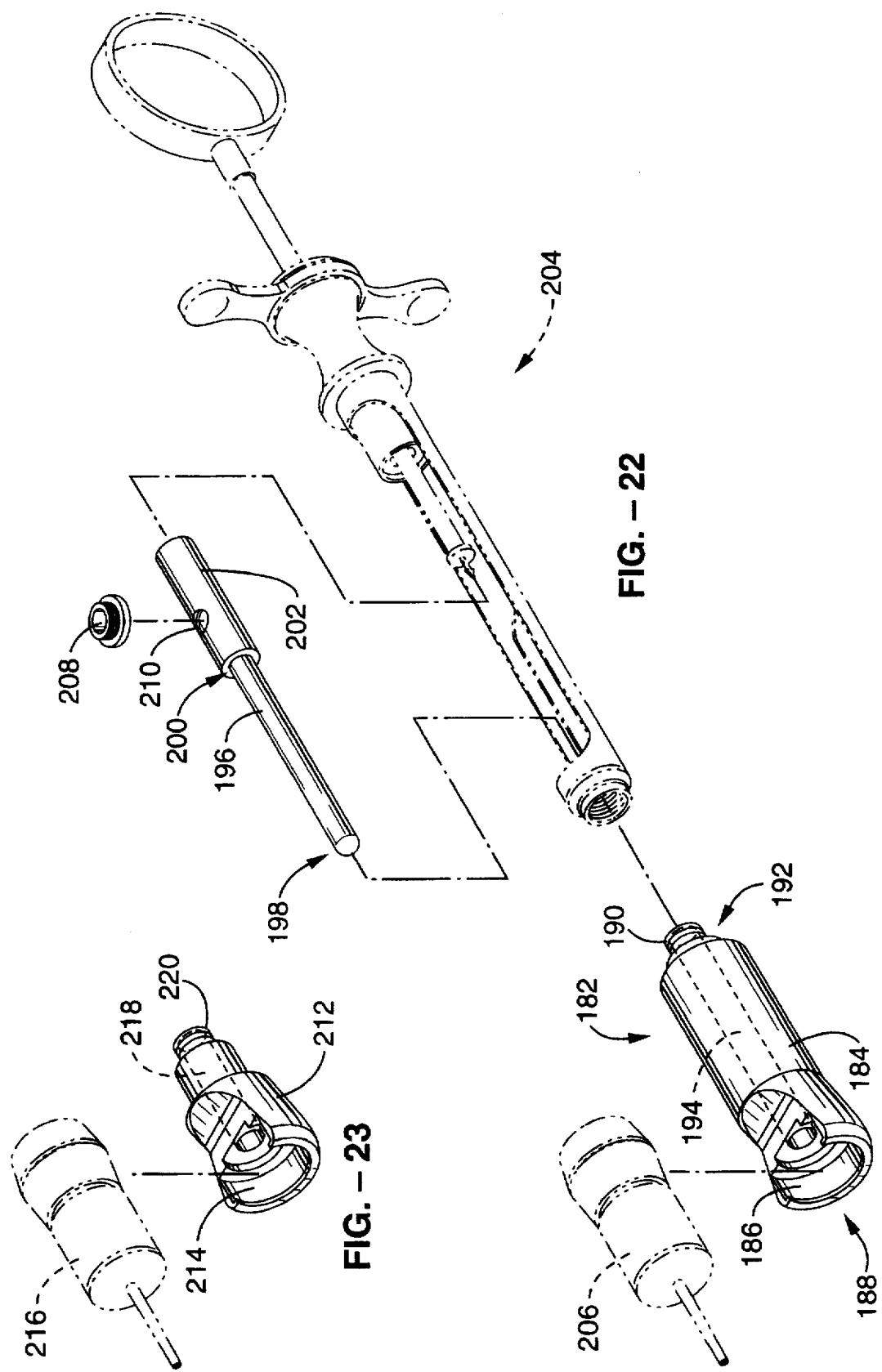

FLUID DISPENSER ADAPTER AND METHOD OF USE

BACKGROUND OF THE INVENTION

1. Field of the Invention

This invention pertains generally to pressure actuated dispensers, applicators and devices for application of fluid materials, and more particularly, to an apparatus which allows conventional dispensing devices to be adapted or modified such that a variety of fluid materials in varying quantities may be dispensed from or applied by a single dispensing device.

2. Description of the Background Art

A large variety of commercial and industrial fluid materials, such as adhesives, lubricants, fillers, sealants, caulking compounds, enchants, polishes, molding compounds and like materials are used in numerous applications. These fluid materials are generally viscous liquids which are frequently available in disposable dispensers or dispensing devices or as disposable cartridges to be used with a dispensing device which accepts the cartridges. Some common examples of dispensing devices include "glue guns" for applying liquid adhesives and "grease guns" for applying liquid lubricants. Such dispensing devices generally involve application of pressure, typically by a manually or hydraulically actuated plunger, onto a reservoir of fluid material to force the material out of the reservoir and through a nozzle, needle, applicator tip, or like exit means. The reservoir of fluid material may be an integral portion of the dispensing device, in which case the entire dispensing device is generally disposed of when the reservoir is depleted. More commonly, the reservoir of fluid material is contained in a cartridge, ampoule, or capsule and, when the reservoir is depleted, the cartridge is removed from the device and replaced with a fresh cartridge.

Since commonly used fluid materials vary in viscosity and chemical properties, different dispenser devices are generally used for dispensing different materials. For example, a "glue gun" is generally not structured and configured to dispense lubricants, and likewise a "grease gun" is generally not compatible with dispensing adhesives. Further, where multiple commercial sources exist for a particular fluid material available in cartridges, such as an adhesive or filler material, the different commercial sources generally provide different dispensing devices which are not compatible with the cartridges from other commercial sources. Thus, an important drawback in currently used dispensing devices is that the users of such fluid materials must generally purchase different dispensing devices for different types of fluid material used, and generally must purchase different dispensing devices for different commercial sources of the same material. This deficiency causes additional expense and adds to the cost of the goods and services ultimately produced.

The drawback of requiring multiple dispensing devices for multiple fluid materials and the multiple commercial sources therefor is perhaps most readily apparent in the dental and orthodontic professions, wherein a large number of liquid adhesive, filler, and other materials used for repair and restorative work are applied by various dispensing devices. Fluid materials such as glass ionomer compounds, resins, sealants, de-sensitizing agents, disinfecting agents, astringents, coagulants, chelating agents, amalgams, cements, porcelain cements, micro- and macro-fill composites and hybrid composites are used for numerous applications, including crowns, temporary and long-term fillings, bridgework, inlays, onlays, posts, pins, cast cores, cast crowns, orthodontic bands, and other applications. In endodontic dental applications, gutta percha or natural rubber is used as a filler for replacing the root or pulp material in root canal procedures. Also frequently used for dental and orthodontic applications are impression materials such as polyether, alginate, rubber, silicones, hydrocolloid, polysulfite and poly vinyl siloxane. All of the aforementioned materials are generally available as viscous fluids or extrudable pastes and compounds that are packaged in disposable capsules, ampules, cartridges, or "compules", which are generally dispensed through a tip applicator by means of special dispensing devices designed to receive a particular type or shape of cartridge. The dispensing devices are frequently pistol-like hand actuated dispensers which accept cartridges or capsules for a particular type and/or commercial brand of fluid material, and which apply pressure to cartridges by means of a plunger.

In the dental and orthodontic professions, the cost of the individual dispensing devices is fairly high, and the large variety of different materials used by dentists requires that a large number of different dispensing devices be purchased by each dental professional. The need for multiple dispensing devices results in additional expense and inconvenience to dentists and orthodontists and adds to the cost of patient treatment. The need for multiple dispensing device additionally creates a clutter problem because numerous dispensing devices need to be on hand for each dental procedure. Yet another problem associated with currently used dispensing devices in the dental and orthodontic professions is that the devices, which quickly become dirty or contaminated, are generally made of non-autoclavable materials and thus are difficult to clean and sterilize and must be frequently replaced, further increasing the ultimate cost of treatment. Further, the currently available devices which are autoclavable tend to degrade, break down or deteriorate through repeated sterilizations, and are prone to corrosion as well, and thus have life expectancies which are greatly reduced.

Accordingly, there is a need for a fluid dispenser adapter apparatus and method which provides for the dispensing of many types of fluid materials from a single dispensing device, which is simple and inexpensive, which is autoclavable, which suffers less wear and tear and is not prone to degradation or corrosion, and which eliminates the need for purchasing and maintaining multiple syringe devices for use with different materials. The present invention satisfies these needs, as well as others, and generally overcomes the deficiencies found in the background art.

The foregoing reflects the state of the art of which the applicant is aware and are tendered with the view toward discharging applicant's acknowledged duty of candor in disclosing information which may be pertinent in the examination of this application. It is respectfully stipulated, however, that the aforementioned background art does not teach or render obvious applicant's claimed invention.

SUMMARY OF THE INVENTION

The present invention pertains to a fluid dispenser adapter apparatus and method which allows the dispensation of multiple types of fluid materials such as pastes, gels, and the like from different commercial sources with the use of a single dispensing device. In its most general terms, the invention comprises a cartridge holder, a movable plunger associated with the cartridge holder, means for transferring force or pressure from a dispensing device to the plunger, and means for coupling the cartridge holder to a dispensing device.

By way of example and not of limitation, the cartridge holder or cartridge holding member includes a first end wherein a partially enclosed chamber, socket, or recessed area is located for interchangeably receiving and holding cartridges of fluid material. The structure and configuration of the socket may be varied to accommodate different types of cartridges or capsules for different types of fluid materials and cartridges from different commercial sources. A longitudinal bore in the cartridge holder, which communicates with the socket, slidably accommodates the plunger. A first end of the plunger is preferably structured and configured to apply pressure on a reservoir portion of a cartridge held in the socket of the cartridge holder, and the means for transferring pressure from a dispensing device is generally associated with a second end of the plunger. In its simplest form, the transferring means may comprise a flat surface on the second end of the plunger structured and configured to receive pressure applied by a piston or other pressure-applying member associated with a standard dispensing device. Alternatively, a shank may be included at the second end of the plunger, and the transferring means may comprise a longitudinal bore within the shank for receiving a piston on a dispensing device. Means for retaining the plunger within the bore of the cartridge holder may also be included with the invention. The means for coupling the cartridge holder to a dispensing device is preferably associated with a second end of the cartridge holder, and may comprise an externally threaded portion for attachment to a dispensing device. The coupling means may also comprise a bayonet mounting arrangement or other quick release arrangement for quick and facile interchanging of dispenser adapters on a dispensing device. Snap-fitting type coupling means, frictional coupling means, and other conventional coupling means are also contemplated for use with the invention.

A conventional dispensing device which generally can only dispense or apply material from a single type or shape of cartridge, may be modified by attachment of the dispenser adapter of the invention to allow different types of cartridges, and thus different fluid materials from different commercial sources, to be dispensed from the same conventional dispensing apparatus. Different dispenser adapters, wherein the cartridge holder of each different dispenser adapter is structured and configured to receive cartridges of different types of fluid materials and or materials from different commercial sources, provide for dispensing or application of multiple materials from a single dispensing device. The length and shape of the dispenser adapter may be varied as required for different applications. Dispensing of large or small volume cartridges may be carried out with the same dispensing device by use of different dispenser adapter with the dispensing device. Since the dispenser adapter comprising the invention is simple and inexpensive to manufacture, the use of multiple dispenser adapter with a single standard dispensing device provides a substantial commercial benefit over the use of multiple dispensing devices. The position and orientation of the cartridge may be adjusted by turning or rotating the cartridge holder relative to the dispensing device, allowing greater accuracy in applying fluid materials. Currently available dispensing devices, in contrast, hold fluid material cartridges locked in place do not allow the accuracy obtainable with the present invention.

The method of utilizing the present invention, in general terms, comprises the steps of coupling a dispenser adapter to a dispensing device, transferring pressure from the dispensing device to the plunger of the dispenser adapter, and forcing fluid material from a cartridge in the dispenser adapter by means of the plunger. The steps of inserting a cartridge of fluid material into the cartridge holder of the dispenser adapter, and the replacing of spent or depleted cartridges, are also generally included with the invention.

The method of using the invention is generally carried out by coupling the dispenser adapter onto a standard dispensing device in a position such that pressure from the dispensing device is transferred to the plunger associated with the cartridge holder of the invention. For dispensing devices wherein manually or hydraulically actuated pistons are involved, the dispenser adapter is generally coupled to the dispensing device in a manner such that the piston of the dispensing device interfaces mechanically with the plunger of the dispenser adapter. A cartridge of fluid material is then inserted into the socket of the cartridge holder and positioned so that pressure from the plunger will empty the cartridge. Thus, by using the standard dispensing device, fluid material is dispensed from the cartridge in the dispenser adapter. A replaceable tip applicator may be included on the cartridge holder to facilitate dispensing of materials with the dispenser adapter. When the plunger has forced all of the fluid material out of the cartridge, the empty cartridge is removed and replaced with a fresh cartridge. A different fluid material may be dispensed from the dispensing device by uncoupling the dispenser adapter from the dispensing device, and attaching a different dispenser adapter which is structured and configured to accommodate cartridges of the different material. The parts of the invention may be made of autoclavable, corrosion-resistant metal and/or polymeric material to provide long service lifetime even with repeated autoclaving. The invention may alternatively be fabricated from inexpensive polymeric material and used as a disposable apparatus. The cartridge holder and plunger of the invention may also be fabricated from flexible or resilient polymeric materials to allow bending or twisting of the apparatus for more accurate application of fluid materials. An anti-slip coating my be included on the dispenser adapter allows users to handle the invention while wearing latex gloves. An anti-stick coating may be included on the plunger and cartridge holder of the invention to prevent adhesives and other sticky materials from causing jamming, which is a drawback present in currently available dispensing devices. Since the invention is simple to use and is utilized with conventional dispensing devices, persons Using the invention will not need to become familiar with a large number of different types of dispensing devices.

The dispenser adapter comprising the invention may be employed in dental, orthodontic, medical, veterinary, and other clinical and laboratory fields by utilizing conventional syringe devices such as aspirating or intraligamental anesthetic syringes which are typically possessed by persons in the above professions. The invention is thus employed by removing the needle from the end of the syringe, and coupling the cartridge holder thereon. The plunger in the cartridge holder is interfaced with the piston of the syringe so that actuation of the syringe piston will actuate the plunger in the cartridge holder. A cartridge is engaged within the socket of the cartridge holder, preferably by snap fitting or other standard means, and a tip applicator is attached to the cartridge (if required). Then, the material within the cartridge is dispensed by manually actuating the syringe piston in a standard manner. Different dispenser adapters may be used to accommodate different types of material capsules or cartridges with the same syringe, thereby eliminating the need for multiple syringe devices for dispensing different types and commercial sources of materials used in the aforementioned professions. The dispenser adapter may be fabricated from autoclavable metallic and/or polymeric materials for easy sterilization for re-use.

An object of the invention is to provide a dispenser adapter which allows the dispensing of multiple fluid materials from a single dispensing device.

Another object of the invention is to provide a dispenser adapter which is easily interchangeable.

Another object of the invention is to provide a dispenser adapter which allows dispensing of fluid materials from multiple commercial sources.

Another object of the invention is to provide a dispenser adapter which is autoclavable and reusable.

Another object of the invention is to provide a dispenser adapter which is simple and easy to use.

Another object of the invention is to provide a dispenser adapter which has few moving parts and thus is not susceptible to breakage and does not require repair.

Another object of the invention is to provide a dispenser adapter which eliminates the clutter associated with use of multiple dispensing devices for a single operation or procedure.

Another object of the invention is to provide a dispenser adapter which is resistant to wear, deterioration, degradation and corrosion.

Another object of the invention is to provide a dispenser adapter which may be fabricated from inexpensive materials to provide a disposable apparatus.

Another object of the invention is to provide a dispenser adapter which allows application of materials in multiple directions through turning or rotation of a cartridge holder.

Another object of the invention is to provide a dispenser adapter which provides for multiple lengths to allow precision application of fluid materials.

Another object of the invention is to provide a dispenser adapter which may be fabricated from flexible or resilient polymeric material to allow increased accuracy in applying fluid materials.

Further objects of the invention will be brought out in the following portions of the specification, wherein the detailed description is for the purpose of fully disclosing the invention without placing limits thereon.

BRIEF DESCRIPTION OF THE DRAWINGS

The invention will be more fully understood by reference to the following drawings which are for illustrative purposes only:

FIG. 1 is a perspective view of a first embodiment of a dispenser adapter in accordance with the present invention, coupled to a conventional pistol-type dispensing device and a replaceable cartridge shown in phantom.

FIG. 2 is an exploded view of the assembly shown in FIG. 1.

FIG. 3 is a perspective view of the dispenser adapter shown in FIG. 1 and FIG. 2.

FIG. 4 is a cross-sectional view of the dispenser adapter shown in FIG. 3 taken through line 4—4.

FIG. 5 is a perspective view of the dispenser adapter shown in FIG. 1 through FIG. 4, showing the plunger extended into the socket of the cartridge holder.

FIG. 6 is a top plan view of the dispenser adapter shown in FIG. 1 through FIG. 5.

FIG. 7 is a perspective view of a second embodiment of a dispenser adapter in accordance with the present invention.

FIG. 8 is a top plan view of the dispenser adapter shown in FIG. 7.

FIG. 10 is an exploded view of the assembly shown in FIG. 9.

FIG. 11 is a perspective view of the dispenser adapter shown in FIG. 9 and FIG. 10.

FIG. 12 is a cross-sectional view of the dispenser adapter shown in FIG. 11 taken through line 12—12.

FIG. 13 is a top plan view of the dispenser adapter of FIG. 9 through FIG. 12.

FIG. 14 is a perspective view of the dispenser adapter shown FIG. 9 through FIG. 13, showing the plunger extended into the socket of the cartridge holder.

FIG. 15 is a perspective view of a fourth embodiment of a dispenser adapter in accordance with the present invention.

FIG. 16 is a top plan view of the dispenser adapter shown in FIG. 15.

FIG. 19 is a cross-sectional view of the plunger and attached shank portion of the dispenser adapter shown in FIG. 18, taken through line 19—19.

FIG. 20 is a perspective view of an alternative embodiment of the cartridge holder shown in FIG. 17 through FIG. 19.

FIG. 21 is a perspective view of a sixth embodiment of a dispenser adapter apparatus in accordance with the present invention coupled to a conventional syringe-type dispensing device and a replaceable cartridge shown in phantom.

FIG. 22 is an exploded view of the assembly shown in FIG. 21.

FIG. 23 is a perspective view of an alternative embodiment of the cartridge holder shown in FIG. 21 and FIG. 22.

DESCRIPTION OF THE PREFERRED EMBODIMENTS

Figure 24:
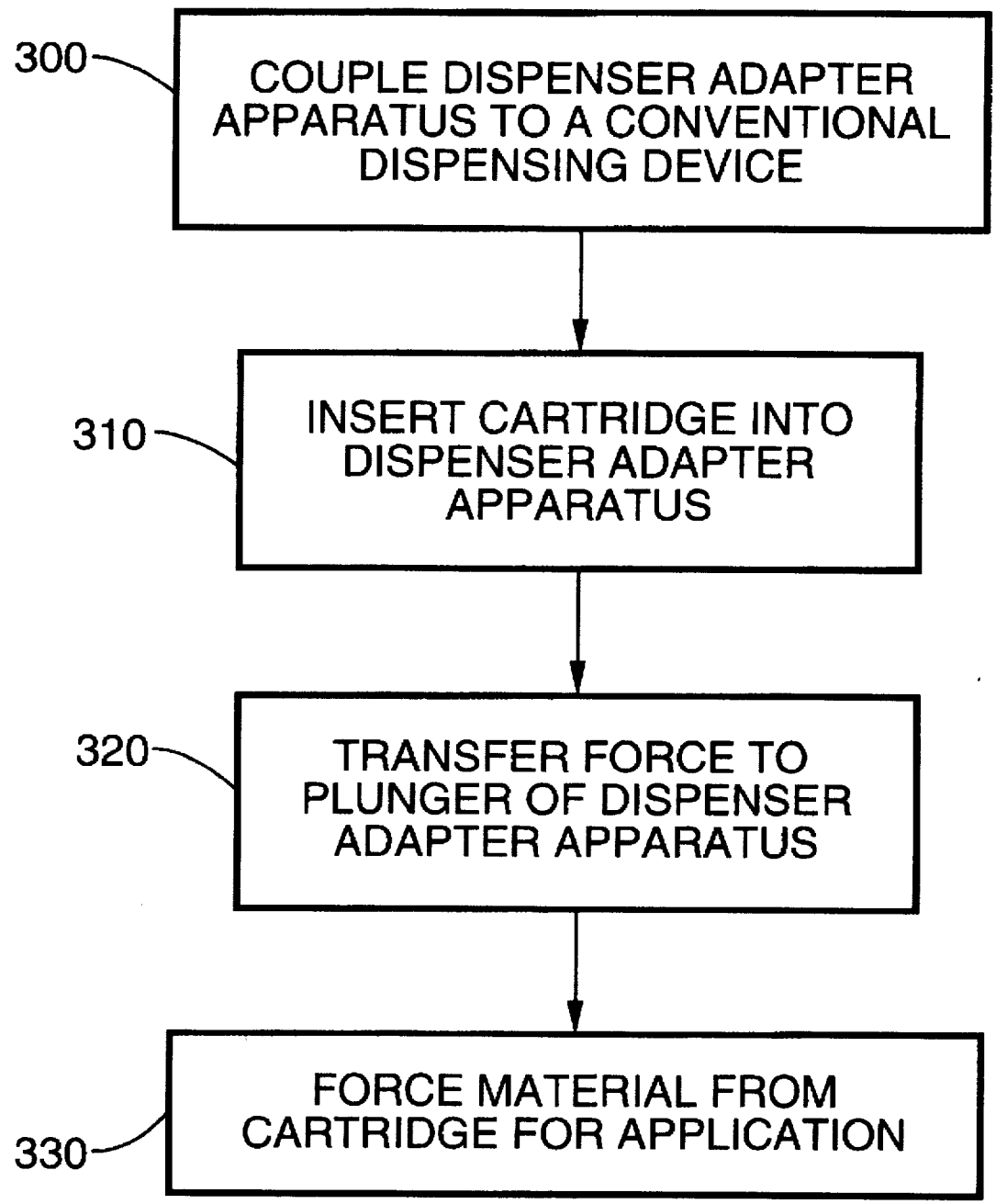
FIG. 24 is a flow chart showing generally the steps of the method comprising the present invention.

Referring more specifically to the drawings, for illustrative purposes the present invention is embodied in the apparatus which is generally shown in FIG. 1 through FIG. 23, and the method which is generally shown in FIG. 24. It will be appreciated that the apparatus may vary as to configuration and as to details of parts, and that the method may vary as to the steps and their sequence, without departing from the basic concepts as disclosed herein. Thus, the following detailed description is merely exemplary, and should not be considered limiting.

For reasons of clarity, the present invention is described in this disclosure in terms of use with hand-actuated, syringe-type dispensing devices as are commonly utilized in dental, medical, veterinary, clinical, and laboratory applications, and the use of the invention is related generally in terms of dental applications. However, as should be readily apparent to persons of ordinary skill in the art, the dispenser adapter of the present invention may be used with a large variety of dispensing devices in a number of applications. Thus, the term "dispensing device" as used herein means generally any device wherein pressure-actuated dispensation of fluid materials is carried out. The dispensing devices suitable for use with the present invention generally will comprise a manually actuated piston or plunger which applies force or pressure. However, dispensing devices which apply force by hydraulic and other means may also be used with the invention. The term "fluid material" as used herein refers generally to all types of liquids, pastes, gels, slurries, powders and like materials which may be dispensed, applied, squeezed or extruded through a nozzle or applicator by application of pressure.

Referring first to FIG. 1 through FIG. 6, there is shown generally a first embodiment 10 of a dispenser adapter in accordance with the present invention, coupled to a conventional pistol-type dispensing device 12 shown in phantom. Dispensing device 12, which is merely one of a variety of types of dispensing devices contemplated for use with the present invention, operates in a standard fashion wherein a piston 14 is incrementally advanced by means of a ratchet and pawl mechanism. Actuation of trigger 16 on dispensing device 12 mechanically actuates pawl 18 by conventional means, allowing piston 14 to move in increments defined generally by sloped notches 20 along piston 14. The dispensing device 12 shown in FIG. 1 and FIG. 2 is typical of those commercially available from the Miltex Company for use as an intraligamental syringe. Similar dispensing devices may be obtained from several sources.

Dispenser adapter 10 comprises a cartridge holder or cartridge holding member 22 having a first end 24 and a second end 26. A partially enclosed cavity, chamber, socket or recessed area 28 adjacent first end 24 defines an opening that is structured and configured to receive an interchangeable and replaceable capsule, ampule, compule, or cartridge 30 which contains fluid material to be dispensed. Socket 28 opens up to the side of cartridge holder 28 as well as first end 24 of cartridge holder, to facilitate interchanging of cartridges 30. Cartridge 30 engages socket 28 of cartridge holder 22 by snap fitting or other conventional means, and is retained therein by friction or other means. As related above, different types of fluid materials, such as adhesives, lubricants, sealants, and fillers are generally available in cartridges of different sizes and shapes, and different commercial sources for such materials tend to provide cartridges in varying sizes and shapes. Accordingly, the size and shape of cavity or socket 28 and cartridge holder 22 may be varied in order to accommodate any type of cartridge. FIG. 1 and FIG. 2 show socket 28 in cartridge holder 22 in a preferred structure and configuration for receiving standard compules or cartridges 30 of multi-component adhesive or filler compounds which are commonly used in the dental profession. The length and shape of cartridge holder 22 may be varied to accommodate particular dispensing operations. For example, a longer, barrel shaped cartridge holder 22 as shown in FIG. 1 through FIG. 6 may be used for posterior dental applications, while a shorter cartridge holder as shown in FIG. 7 and FIG. 8 may be used for anterior dental applications, as discussed further below.

The present invention also comprises a plunger or rod 32 associated with cartridge holder 22. Preferably, a longitudinal bore 34 in cartridge holder 22 slidably accommodates plunger 32. Plunger 32 is preferably elongated in shape and of generally cylindrical structure and configuration, although a variety of plunger shapes and configurations are suitable for use with the invention. Plunger 32 includes a first end 36 and a second end 38 (FIG. 4), with the first end of plunger 32 generally adjacent to socket 28 in cartridge holder 22. A shank portion 40 (FIG. 4) may be included on plunger 32 adjacent second end 38 of plunger 32. First end 36 of plunger 32 is generally structured and configured to apply pressure to cartridge 30 during extension so that the fluid material contained therein is discharged from the cartridge 30, is described further below.

Means for coupling cartridge holder 22 to a dispensing device are also included with the invention. Preferably, the coupling means comprises a threaded portion 42 adjacent second end 26 of cartridge holder 22, through which longitudinal bore 34 extends. Threaded portion 42, while shown as externally threaded, may be internally threaded or otherwise suitably structured and configured for coupling to a conventional dispensing device such as dispensing device 12. The coupling means could alternatively comprise a, snap fitting arrangement, frictional means, bayonet mounting, conventional quick release fittings, or any other coupling means commonly used in the art. Threaded portion 42 may itself be detachable, so that the coupling means of the invention may be interchanged, allowing attachment of the dispenser adapter apparatus 10 to a variety of dispensing devices.

Means for retaining plunger 32 in bore 34 of cartridge holder may be included with the invention, to prevent loss of plunger 32 and otherwise minimize inconvenience. As shown in FIG. 4, the retaining means preferably comprises an inwardly disposed lip 44 within bore 34 adjacent threaded portion 42, and an inwardly disposed lip or shoulder 46 within bore 34 adjacent socket 28, which prevent shank portion 40 on plunger 32 from sliding or slipping out of bore 34.

Also provided with the invention are means for transferring force or pressure from a dispensing device to the plunger 32 of dispenser apparatus 10. In the embodiment of the invention shown generally in FIG. 1 through FIG. 6, the transferring means preferably comprises a flat surface 48 (FIG. 4) on shank portion 40 which is structured and configured to interface with a flat end 50 (FIG. 2) on piston 14 of dispensing device 12. The transferring means employed with the invention, however, will generally vary with the types of dispensing devices utilized with the invention. For example, use of the invention with dispensing devices having pistons which do not include a flat end will generally require different means for interfacing with the piston of the dispensing device, as discussed further below in another embodiment of the invention.

The dispenser adapter 10 is utilized generally by coupling the cartridge holder 22 to dispensing device 12 by engaging threaded portion 42 with an internally threaded socket 52 (FIG. 2) on dispensing device 12, with flat end 50 of piston adjacent to flat surface 48 on shank portion 40. Traction means, such as a plurality of longitudinal ridges or serrations (not shown) may be included on cartridge holder 22 to facilitate handling. A compule or cartridge 30 of fluid material to be dispensed is then placed into socket 28 and securely engaged therein by friction, snap fitting, or other means. A user then grasps handle 54 on dispensing device 12, and actuates trigger 16 by applying force or pressure to, thereby moving or advancing piston 14 incrementally forward. Since piston 14 and plunger 32 are interfaced by contact of flat end 50 of plunger and flat surface 48 on shank portion 40 of plunger 32, force or pressure is transferred to plunger 32 from piston 14, and plunger 32 slides or otherwise moves forward within bore 34 towards cartridge 30 as piston 14 moves forward. The pressure applied by first end 36 of plunger 32 on cartridge 30 forces the fluid material out of cartridge 30 and through tip applicator 56. Plunger 32 generally penetrates cartridge 30 and proceeds through cartridge 30 while forcing the discharge of materials therefrom. When cartridge 30 is spent or empty, piston 14 on dispensing device 12 is retracted, plunger 32 is disengaged from cartridge 30, and the spent cartridge may be replaced with a fresh cartridge. If the user wishes to use dispensing device 12 for dispensing another type of material in a different type of cartridge, then the dispenser adapter 10 is disengaged from dispensing device 12, and another dispenser adapter which is suitably structured and configured for the different cartridge is coupled to the dispensing device 12, and used in generally the same manner.

Referring next to FIG. 7 and FIG. 8, there is shown a second embodiment of a dispenser adapter 58 in accordance with the invention. The dispenser adapter apparatus 58 includes a cartridge holder 60 with a cavity or socket 62, and a plunger 64 within a bore 66, and in general is identical to the dispenser adapter apparatus 10 described above except for the length and shape of the cartridge holder 60. The cartridge holder 60 of dispenser adapter apparatus 58 is substantially shorter in length than described above, to provide for use of the invention in different applications. In the dental profession, for example, the longer first embodiment dispenser adapter 10 is more suitable for posterior dental operations which require dispensing of fluid materials such as adhesives and filler compounds, while the second embodiment dispenser adapter 58 is more suitable for anterior dental applications. A cartridge 68 with an angled applicator tip 70 is shown in phantom in FIG. 7 with dispenser adapter 58. Cartridge 68 is shown with a structure and configuration which is standard in the dental profession. The dispenser adapter 58 may be used interchangeably with dispenser adapter 10 on the same dispensing device 12, allowing the dispensing or application of different fluid materials from different types of cartridges with the same dispensing device 12 by merely changing the dispenser adapter. When the invention is used with an angled applicator tip as shown in FIG. 7, the direction of fluid material application may be precision adjusted by rotating or turning cartridge holder relative to the attached dispensing device.

Referring now to FIG. 9 through FIG. 14, them is shown a third embodiment of a dispenser adapter 72 in accordance with the present invention. Like the first and second embodiments of the invention described above, dispenser adapter 72 comprises a cartridge holding member or cartridge holder 74, with a partially enclosed chamber or socket 76 adjacent a first end 78, and coupling means in the form of a threaded portion 80 adjacent a second end 82. A longitudinal bore 84 extends along the length of cartridge holder 74 and threaded portion 80, and opens into socket 76. A plunger 86 having first and second ends 88, 90 (FIG. 12) respectively is slidably accommodated within bore 84. Means for transferring force or pressure from a dispensing device is shown as a flat surface 92 on a shank portion 94 (FIG. 12) associated with second end 90 of plunger 86. Retaining means in the form of lip 96 and shoulder 98 (FIG. 12) within bore 84 prevent shank portion 94 and thus plunger 86 from exiting bore 84.

Figure 9:
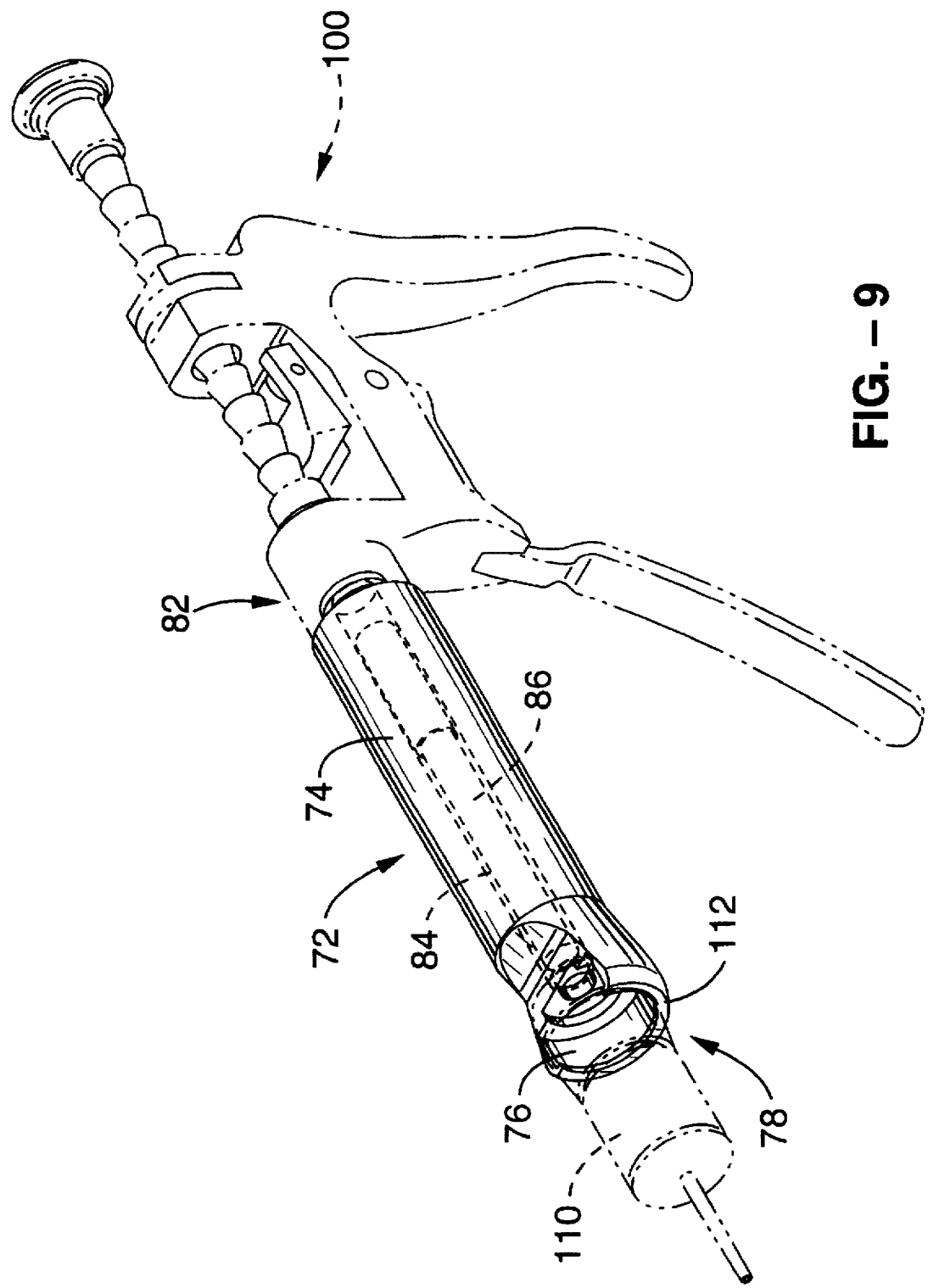
FIG. 9 is a perspective view of a third embodiment of a dispenser adapter in accordance with the invention, coupled to a conventional pistol-type dispensing device and a replaceable cartridge shown in phantom.

The dispenser adapter 72 comprising the third embodiment of the invention is used in generally the same manner with a conventional dispensing device 100 as described above, with threaded portion 80 engaging a threaded socket 102 (FIG. 10) on dispensing device 100, and flat surface 92 on shank portion 94 abutting or interfacing with a flat end 104 (FIG. 10) on piston 106 of dispensing device 100. Ridges, serrations or the like (not shown) may be included on cartridge holder 74 to facilitate handling or manipulation thereof. A compule or cartridge 110 is engaged within socket 76, and material is dispensed therefrom as described above. The dispenser adapter 72 comprising the third embodiment of the invention is described primarily to show that a variety of structures and configurations for socket 76 and cartridge holder 72 are contemplated for use with the present invention. The cartridge 110 shown in FIG. 9 and FIG. 10 is shown with a structure and configuration similar to a standard compule or cartridge configuration used in the dental profession for glass-ionomer restorative material. To accommodate cartridge 110, a partially encircling flange 112 extends outward at first end 78 of cartridge holder 74 to further define socket 76.

Referring next to FIG. 15 and FIG. 16, there is shown generally a fourth embodiment of a dispenser adapter 114 in accordance with the present invention. The dispenser adapter 114 includes a cartridge holder 116 with a cavity or socket 118 therein, and a plunger 120 slidably mounted within a bore 122 in cartridge holder 116, and in general is identical to the dispenser adapter 72 as described above except for the length and shape of the cartridge holder 116. The cartridge holder 116 of dispenser adapter 114 is shorter in length to provide for use of the invention in different applications, as described above for the second embodiment of the invention. Particularly, the dispenser adapter 114 illustrates a preferred embodiment of the invention for applying translucent glass-ionomer filler compound for anterior dental restorative work.

Figure 17:
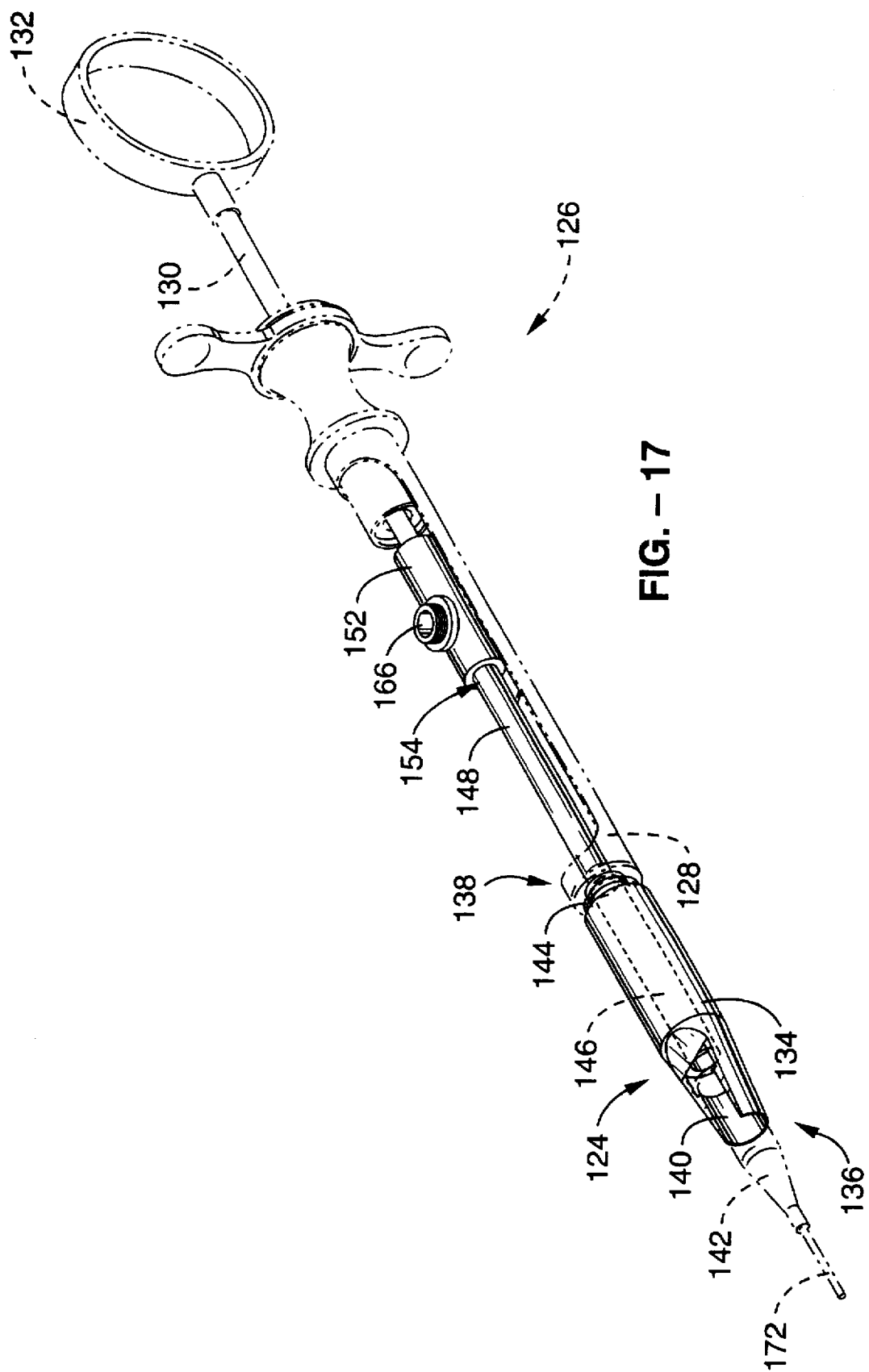
FIG. 17 is a perspective view of a fifth embodiment of a dispenser adapter in accordance with the present invention, coupled to a conventional syringe-type dispensing device and a replaceable cartridge shown in phantom.
Figure 18:
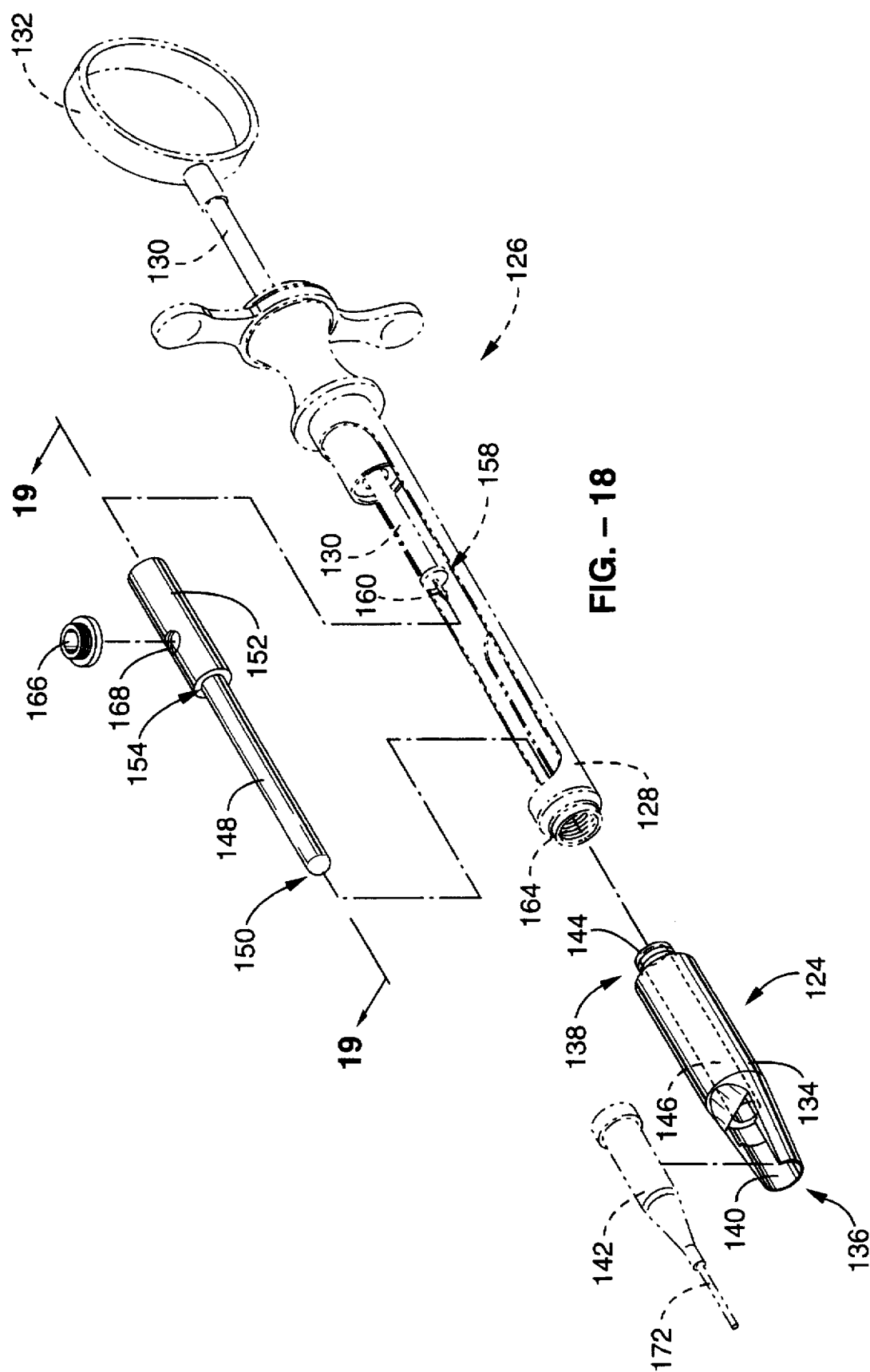
FIG. 18 is an exploded view of the assembly shown in FIG. 17.

Shown in FIG. 17 through FIG. 19 is a fifth embodiment of a dispenser adapter 124 in accordance with the invention. Dispenser adapter 124 is generally structured and configured to be used with a conventional syringe type dispensing device, shown as a standard aspirating syringe 126, as is commonly used for administering anesthetics or injection of medication. Syringe 126 includes generally a body portion 128 and an elongated piston 130 slidably extending therethrough. A ring 132 on piston 130 accommodates a user's thumb (not shown), so that pressure may be applied to piston 130 in a manner well understood in the art.

Dispenser adapter 124 comprises a cartridge holder 134 with first and second ends 136, 138 respectively. A recessed area or socket 140 for receiving a cartridge 142 is provided adjacent first end 136 of cartridge holder 134, and coupling means, preferably in the form of a threaded portion 144, are associated with the second end 138. As in the other embodiments of the invention described herein, other coupling means, including different external or internal threaded arrangements, snap fitting, frictional attachment, or other standard coupling means are also contemplated for use in coupling the apparatus 124 to a syringe 126 or other dispensing devices. A longitudinal bore 146 extends the length of cartridge holder 134 and threaded portion 144, and slidably accommodates a plunger 148 having a rounded first end 150 and shank portion 152 adjacent to a second end 154. Means for transferring pressure or force from piston 130 of syringe 126 to plunger 148 preferably comprises an aperture or bore 156 (FIG. 19) in the shank portion 152 of plunger 148, which engages or interfaces with the end 158 (FIG. 18) of syringe piston 130. Since many conventional syringes include a barb or prong 160 on piston end 158, bore 156 in shank portion 152 preferably includes an opening 162 (FIG. 19) to accommodate barb 160 and prevent the breaking or dulling of the point of barb 160. As discussed above, other transferring means for interfacing plunger 148 and syringe piston 130 are contemplated for use with the invention, depending generally on the structure and configuration of the piston of the dispensing device utilized with the invention.

Dispenser adapter 124 is utilized generally by disengaging plunger 148 from bore 146 in cartridge holder 134, and placing plunger 148 within the body 128 of syringe 126, and engaging piston end 158 in bore 156 of shank portion 152, with barb 160 accommodated in opening 162. Cartridge holder 134 is coupled to syringe 126 by engaging threaded portion 144 into a threaded socket 164 (FIG. 18) on syringe body 128. Since standard syringes generally include a needle adapter 166 for using interchangeable needles with syringe 126, the invention includes retention means for holding a needle adapter 166 while syringe 126 is used with the dispenser adapter apparatus 124. Preferably, the retention means comprises a threaded hole 168 in shank portion 152 of plunger 148, so that needle adapter 166 can be threadedly attached thereto by a threaded portion 170 (FIG. 19) and retained for future use without the risk of misplacement while syringe 126 is used with the dispenser adapter 124. A cartridge 142 is fitted within socket 140 and held therein by snap fitting, friction or other standard means, as described above. Then, by applying force to syringe piston 130 in a standard manner, plunger 148 is moved forward, sliding through bore 146 and into cartridge 142, applying pressure thereto and causing discharge of the fluid contents held therein through applicator tip 172. As described above, spent cartridges may be removed and replaced, or different dispenser adapter apparatus may be coupled to syringe 126 for dispensing different materials from different cartridges.

Referring next to FIG. 20, there is shown an alternative embodiment of a cartridge holder 174. Cartridge holder 174 includes a socket 176 for receiving a cartridge 178, and a bore 180 which accommodates a plunger (not shown). Cartridge holder 174 is used in an identical manner as described above for the dispenser adapter 124. Cartridge holder 174 is disclosed primarily to illustrate that a large variety of structures and configurations for the cartridge holder of the invention are possible and are contemplated for use with the invention. Cartridge holder 174 is relatively small compared to the size of socket 176, such that socket 176 comprises the bulk of cartridge holder 174. The short length of cartridge holder 174 makes it particularly suitable for anterior dental procedures, while dispenser adapter apparatus 124 as described above is more suitable for posterior dental applications. Thus, application of adhesives, fillers, and other compounds used in the dental profession may be carried out entirely with the use of a conventional syringe, eliminating the need for multiple dispensing devices.

Referring now to FIG. 21 and FIG. 22, there is shown generally a sixth embodiment of a dispenser adapter 182 in accordance with the invention. As in the other embodiments described above, dispenser adapter 182 comprises a cartridge holding member or cartridge holder 184, with a partially enclosed chamber or socket 186 adjacent a first end 188, and coupling means in the form of a threaded portion 190 adjacent a second end 192. A longitudinal bore 194 extends along the length of cartridge holder 184 and threaded portion 190, and opens into socket 186. A detachable plunger 196 having first and second ends 198, 200 respectively is slidably accommodated within bore 192. Means for transferring force or pressure from a syringe or other dispensing device preferably comprise a shank portion 202 on second end 200 of plunger, with a bore (not shown) as generally described above for the fifth embodiment of the dispenser adapter 124.

The dispenser adapter 182 is used in generally an identical manner with a conventional syringe 204 as related for dispenser adapter 124 above. Dispenser adapter 182 differs from dispenser adapter 124 primarily in the shape of socket 184 and cartridge holder 182, which is structured and configured to receive cartridge 206, which, as related earlier is of a structure and configuration commonly used with glass-ionomer filler compound for dental applications. A needle adapter 208 may be held in bore 210 in shank portion 202 as described above. Dispenser adapter 182 is disclosed to show that a variety of cartridge holder and socket configurations may be utilized with the invention to accommodate a variety of types of cartridges.

In FIG. 23 there is shown an alternative embodiment of a cartridge holder 212 which is, of short configuration suitable for anterior dental applications. Cartridge holder 212 includes a socket 214 for receiving cartridge 216, a bore 218 for receiving a plunger (not shown), and a threaded portion 220 for coupling to a dispensing device. The short configuration of cartridge holder 212 is a preferred shape for anterior dental applications.

The method of using the invention will be seen by reference to FIG. 24, wherein a flow chart generally outlining the steps of using the invention is shown. In step 300, a dispenser adapter apparatus is coupled to a conventional dispensing device such as the pistol-type or syringe-type dispensing devices described above. The coupling may be carried out by means of interfitting threaded portions as described above, or by snap fitting, frictional engagement, or any other standard coupling means.

In step 310, a cartridge in inserted into the dispenser adapter apparatus, preferably by engaging the cartridge within a socket in a cartridge holder, as related above.

In step 320, force or pressure is transferred from the dispensing device to a plunger of the dispenser adapter apparatus. As related above, the plunger is generally associated with a cartridge holder by slidably engaging a bore therein. The transfer of force or pressure is generally carried out by interfacing the plunger of the dispenser adapter apparatus with the piston of the dispensing device as discussed above.

In step 330, fluid material is forced from a cartridge held in the cartridge holder of the dispenser adapter apparatus. Generally, the fluid material is forced from the cartridge by the action of the plunger thereupon, as described above, so that material contained within the cartridge may be applied for various applications.

Additional steps may also be utilized with the present invention, including the step of removing a spent cartridge from the cartridge holder apparatus, and replacing it with a fresh cartridge. The step of interchanging different dispenser adapters on the dispensing device may also be included with the invention.

As illustrated by the above embodiments of the invention, it can be seen that a variety of dispenser adapter apparatus may be used interchangeably on a single dispensing device to allow dispensing or application of a variety of fluid materials with a single dispensing device. For example, all of fluid materials used in the dental profession, such as glass ionomer compounds, resins, sealants, de-sensitizing agents, disinfecting agents, astringents, coagulants, chelating agents, amalgams, cements, porcelain cements, micro- and macro-fill composites and hybrid composites may be dispensed or applied with the present invention. The invention thus may used for numerous dental procedures, including crowns, temporary and long-term fillings, bridgework, inlays, onlays, posts, pins, cast cores, cast crowns, orthodontic bands, and other applications. In endodontic dental applications, gutta percha may be dispensed with the invention for replacing the root or pulp material in root canal procedures. Impression materials such as polyether, alginate, rubber, silicones, hydrocolloid, polysulfite and poly vinyl siloxane, may also be dispensed by use of the present invention. Commercially available dental materials which may be dispensed with the invention include, but are not limited to, SUPERDENT, PROTEMP, PHOTAC-FIL, IMPREGUM, PENTA, PERMADYNE, KETAC, MAGNACORE, OPTIBOND, PHOTAC, PRISMA, DYRACT, REPROSIL, NUPRO, DELTON, DENTHESIVE, DURAFILL, ULTRAFIL, HELIOSEAL, MIRACLE MIX, PERTAC, FUJI II, TETRIC, AQUASIL, and TPH. These examples are provided merely to illustrate some of the many fluid materials used in the dental profession which may be dispensed with the present invention.

The dispensing device used with the invention may be a conventional syringe as shown above, and thus dentists using the invention no longer need to purchase multiple dispensing devices for the above materials, but may use their anesthetic syringe, thereby avoiding the additional cost which has heretofore been required for purchasing multiple dispensing devices for application of different fluid materials. Thus, the invention provides a significant reduction in expense for dental professionals which reduces the cost of treatment. The present invention also eliminates the clutter associated with multiple dispensing devices which generally must be on hand for dental procedures, thereby simplifying and facilitating dental procedures.

The dispenser adapter comprising the invention, as used in the dental profession, is preferably fabricated from metal or metal alloy, or natural or man-made polymeric material or composite materials thereof which are heat-resistant, corrosion resistant, and generally resistant to wear, deterioration, and degradation as occurs with many of the currently used dispensing devices, thus allowing for long-term use of the dispenser adapter. Preferably, the cartridge holder and plunger of the dispenser adapter are cast or machined from aluminum, to provide an inexpensive dispenser adapter which is easily autoclavable or otherwise sterilizable for re-use. An anti-stick coating such as HARDCOAT, TEFLON or a like coating may be included on the plunger and cartridge holder surfaces to prevent adhesives or other materials used with the invention from sticking to parts of the apparatus which could otherwise cause jamming as occurs in background art dispensing devices. Anti-slip coating may be included on the exterior of the cartridge holder to facilitate handling of the invention while wearing gloves. It is alternatively contemplated that the invention may be fabricated from inexpensive polymeric materials so that the dispenser adapter comprising the invention is disposable. It is further contemplated that the cartridge holder and plunger of the invention may be fabricated from resilient or flexible materials so that the dispenser adapter may be twisted or bent during use to allow more precision in dispensing or applying materials. As shown above, the dispenser adapter may be made in various lengths to facilitate particular operations. Thus, the invention is particularly well suited to endodontic procedures wherein anesthetics and other medications must be injected with precision.

For application of fluid materials which require heating prior to their dispensation, such as gum percha, a heating element may be included within the cartridge holder, or a heating jacket may be utilized with a cartridge holder to facilitate material application.

In a profession such as dentistry wherein many different materials are to be dispensed and several configurations of the dispenser adapter apparatus and cartridges may be on hand, the individual dispenser adapter apparatus may be color coded for quick identification, so that time is not wasted experimenting to see which cartridge fits with a particular dispenser adapter.

While only two types of dispensing devices are described above in detail for use with the invention, it should be readily understood that the dispenser adapter comprising the invention can be utilized with virtually any type of dispensing device for fluid materials. It is contemplated that the dispenser adapter comprising the invention may be used with gas-operated, air-operated, and hydraulic-operated dispensing devices as well as hand operated dispensing devices as described above. Similarly, while the descriptive examples provided above relate primarily to the field of dentistry, it is contemplated that the invention may be used in a variety of applications. For example, in building or dwelling construction, the dispenser adapter apparatus of the invention will allow the dispensing of multiple adhesives, sealants, and caulks with only a single dispensing device. Likewise, in automotive manufacturing and repair, a variety of sealants, lubricants and adhesives may be dispensed with a single dispensing device through use of the invention. In medical and surgical applications, the invention may be used for administering anesthetics or other drugs.

Accordingly, it will be seen that the present invention provides a dispenser adapter apparatus which allows various types of materials to be dispensed with a single dispensing device. Although the description above contains many specificities, these should not be construed as limiting the scope of the invention but as merely providing illustrations of some of the presently preferred embodiments of this invention. Thus, the scope of the invention should be determined by the appended claims and their legal equivalents.

I claim:

1. A dispenser adapter apparatus, comprising:
   (a) a cartridge holder, said cartridge holder having first and second ends, said cartridge holder having a longitudinal bore between said first and second ends, said cartridge holder including socket means positioned at said first end for lateral insertion and securing of a cartridge containing a fluid material;
   (b) a plunger, said plunger slidably disposed within said bore of said cartridge holder;
   (c) means for coupling said cartridge holder to a dispensing device of the type having a slidable piston, said coupling means positioned adjacent said second end of said cartridge holder: and
   (d) means for transferring force from said slidable piston in said dispensing device to said plunger.

2. A dispenser adapter apparatus as recited in claim 1, wherein said plunger has a first end and a second end, said first end of said plunger positioned adjacent said socket of said cartridge holder, said transferring means associated with said second end of said plunger.

3. A dispenser adapter apparatus as recited in claim 1, further comprising means for retaining said plunger within said bore.

4. A dispenser adapter apparatus as recited in claim 1, wherein said cartridge holder is elongated in shape.

5. A dispenser adapter apparatus as recited in claim 1, wherein said plunger includes a shank portion adjacent said second end of said plunger.

6. A dispenser adapter apparatus as recited in claim 5, wherein said transferring means comprises a bore in said shank portion structured and configured to receive the piston of said dispensing device.

7. A method of dispensing fluid materials using a dispenser adapter as recited in claim 1, comprising the steps of:

(a) coupling said dispenser adapter apparatus to said dispensing device;

(b) transferring force from said dispensing device to said plunger; and (c) forcing fluid material from a cartridge held in said cartridge holder.

8. A method or dispensing fluid materials as recited in claim 7, further comprising the step of placing said cartridge of fluid material within said cartridge holder on said dispenser adapter.

9. A dispenser adapter apparatus, comprising:

(a) a cartridge holder, said cartridge holder including first and second ends, said cartridge holder including a longitudinal bore between said first and second ends, said cartridge holder including a socket positioned adjacent said first end, said socket including means for lateral insertion and securing of a cartridge containing a fluid material;

(b) an elongated plunger, said plunger slidably disposed within said bore in said cartridge holder;

(c) coupling means for attaching said cartridge holder to a dispensing device of the type having a slidable piston, said coupling means located adjacent said second end of said cartridge holder; and (d) interfacing means for transferring pressure from said slidable piston in said dispensing device to said plunger.

10. A dispenser adapter apparatus as recited in claim 9, wherein said plunger has a first end and a second end, said first end of said plunger positioned adjacent said socket of said cartridge holder, said interfacing means positioned adjacent said second end of said plunger.

11. A dispenser adapter apparatus as recited in claim 9, further comprising means for retaining said plunger within said bore.

12. A dispenser adapter apparatus as recited in claim 9, wherein said plunger includes a shank portion adjacent said second end of said plunger.

13. A dispenser adapter apparatus as recited in claim 12, wherein said transferring means comprises a bore in said shank portion, said bore in said shank portion structured and configured to receive a piston in said dispensing device.

14. An adapter, comprising:

(a) a cartridge holder, said cartridge holder having a first end, said cartridge holder having a second end, said cartridge holder including a longitudinal bore extending between said first and second ends, said cartridge holder including a socket adjacent said first end, said socket including means for lateral insertion and securing of a cartridge containing a fluid material;

(b) an elongated plunger, said plunger slidably engaging said bore in said cartridge holder;

(c) coupling means for attaching said cartridge holder to a dispensing device of the type having a slidable piston, said coupling means adjacent said second end of said cartridge holder; and (d) interfacing means for transferring force from said slidable piston in said dispensing device to said plunger.

15. An adapter as recited in claim 14, further comprising means for retaining said plunger within said bore.

16. An adapter as recited in claim 14, wherein said plunger has a first end and a second end, said first end of said plunger positioned adjacent said socket in said cartridge holder, said interfacing means adjacent said second end of said plunger.

17. An adapter as recited in claim 16, wherein said interfacing means comprises a bore included in said shank portion, said bore structured and configured to receive a piston in said dispensing device.

18. An adapter as recited in claim 16, wherein said plunger includes a shank portion, said shank portion positioned adjacent said second end of said plunger.

19. An adapter as recited in claim 18, further comprising retention means for holding a needle adapter for a dispensing device, said retention means included on said shank portion of said plunger.

20. A method of dispensing fluid materials, comprising the steps of:

(a) providing a dispenser adapter, said dispenser adapter comprising a cartridge holder, said dispenser adapter comprising a plunger slidably disposed within a longitudinal bore extending between first and second ends of said cartridge holder, said cartridge holder including socket means positioned at said first end for lateral insertion and securing of a cartridge containing a fluid material;

(b) coupling said dispenser adapter to a dispensing device;

(c) laterally inserting said cartridge of fluid material within said cartridge holder on said dispenser adapter;

(d) transferring force from said dispensing device to said plunger on said dispenser adapter; and (e) forcing, by said plunger, fluid material from said cartridge in said cartridge holder.

21. An adapter, comprising:

(a) a cartridge holder, said cartridge holder having a first end, said cartridge holder having a second end, said cartridge holder including a longitudinal bore, said cartridge holder including a socket adjacent said first end;

(b) an elongated plunger, said plunger slidably engaging said bore in said cartridge holder, said plunger having a first end and a second end, said first end of said plunger positioned adjacent said socket in said cartridge holder, said plunger including a shank portion, said shank portion positioned adjacent said second end of said plunger;

(c) coupling means for attaching said cartridge holder to a dispensing device, said coupling means adjacent said second end of said cartridge holder;

(d) interfacing means for transferring force from a piston in said dispensing device to said plunger, said interfacing means adjacent said second end of said plunger; and (e) retention means for holding a needle adapter for said dispensing device, said retention means included on said shank portion of said plunger.

* * * * *